United States Patent
Rickey, Jr.

[11] Patent Number: 5,520,393
[45] Date of Patent: May 28, 1996

[54] SPATIAL PERCEPTION/PHYSICAL REACTION GAME

[76] Inventor: Alfred J. Rickey, Jr., 1851 NE. 62nd St., Apt. 503, Fort Lauderdale, Fla. 33308

[21] Appl. No.: 254,548

[22] Filed: Jun. 6, 1994

[51] Int. Cl.⁶ ........................................ A63F 3/00
[52] U.S. Cl. .................................. 273/237; 434/258
[58] Field of Search ........................... 273/265, 237, 273/238, 285, 236; 434/258

[56] References Cited

U.S. PATENT DOCUMENTS

| | | | |
|---|---|---|---|
| 1,232,133 | 7/1917 | Warden | 273/238 |
| 2,053,598 | 9/1936 | Blau | 273/265 |
| 2,460,208 | 1/1949 | Zalkind | 273/265 X |
| 2,898,108 | 8/1959 | Meyer | 273/265 X |
| 3,085,803 | 4/1963 | Krzes | 273/265 X |
| 3,376,041 | 4/1968 | Anderson | 273/238 |
| 3,887,189 | 6/1975 | Dawes | 273/238 |
| 4,222,570 | 9/1980 | Gray | 273/265 X |
| 4,231,577 | 11/1980 | Thomas et al. | 273/265 X |
| 4,541,633 | 9/1985 | Newbill | 273/238 |
| 4,550,916 | 11/1985 | Ortiz | 273/265 X |
| 4,616,832 | 10/1986 | Groner | 273/265 X |
| 4,801,148 | 1/1989 | Lamb | 273/265 X |
| 5,013,047 | 5/1991 | Schwab | 273/238 |
| 5,129,654 | 7/1992 | Bogner | 273/238 |
| 5,251,644 | 10/1993 | Fitzgerald | 273/265 X |

FOREIGN PATENT DOCUMENTS

| | | | |
|---|---|---|---|
| 635614 | 9/1936 | Germany | 273/265 |

*Primary Examiner*—William E. Stoll
*Attorney, Agent, or Firm*—Alvin S. Blum

[57] ABSTRACT

A game tests spatial perception in vertical and horizontal planes and physical responsiveness. A vertical planar display displays selected points thereon. A test point is displayed thereon and a player being challenged, upon seeing the test point, must select a response point on a corresponding planar horizontal response panel which is perceived to correspond to the test point position. The response point is then transferred to a corresponding location on the display, so that test and response points are both displayed. The distance between the points is measured as a score. The time interval between viewing the test point and response may also be recorded to be combined with the distance in a score. The horizontal response panel may be a touch sensitive screen. Competing players may each have a response panel shielded from other players.

12 Claims, 1 Drawing Sheet

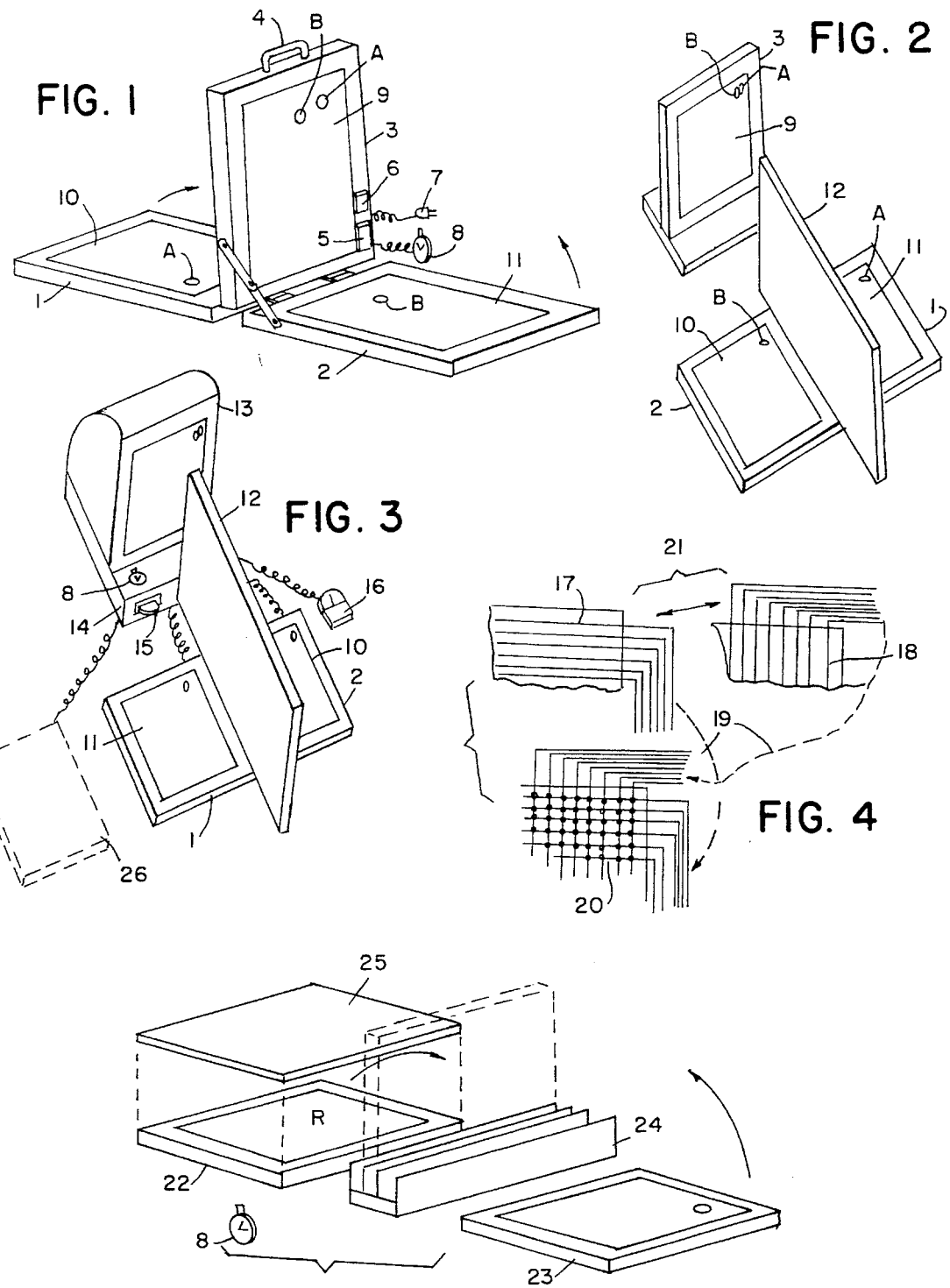

SPATIAL PERCEPTION/PHYSICAL REACTION GAME

BACKGROUND OF THE INVENTION

This invention relates to games of skill in which a player must respond to a point in space, and more particularly to a game in which a player perceives a test point in a vertical display plane and is required to position a response point in a corresponding horizontal response plane as closely as possible to the test point, with position error and response time applied to the score.

There are a variety of military warfare board games of the "salvo" type with vertical and horizontal panels, but they are related to positioning multiple pieces on each panel for strategy games relative to an unseen target. Many sports require a player to respond promptly to fast on-coming balls, punches and the like at any point in space. This action-reaction game could help sharpen an athlete's performance. It may also be useful as therapy for those recovering from a stroke, as well as simply a challenging game of skill. Applicant is not aware of any other game that tests the ability of a player to mentally translate a visible position in a vertical plane to a position in a horizontal plane and then require manual positioning in the horizontal plane.

SUMMARY OF THE INVENTION

It is accordingly an object of the invention to provide a game or training device comprising a planar vertical display panel for displaying a point at any position selected by a first player or tester. Another planar panel, a response panel, of dimensions corresponding to the display panel lies in a horizontal plane for use by the second player or testee. The response panel is touched by the testee at a point judged to correspond to the point seen on the display panel. The system may be constructed to then project the touched point on the test panel onto the vertical panel. The positioning error may then be measured manually or automatically. The time between display and response may also be recorded. A scoring display then displays a score based on a combination of placement error and response time. The prompt visual display of skill may encourage practice and improvement in the perceptual and motor skills involved in the process. Two competing players may alternate displaying and responding with duplicate panels or by sharing panels.

These and other objects, advantages and features of the invention will become more apparent when the detailed discriptions are considered in conjunction with the drawings.

BRIEF DESCRIPTION OF THE DRAWINGS

FIG. 1 is a perspective view of the game of the invention.

FIG. 2 is a perspective view of another embodiment of the game of the invention.

FIG. 3 is a perspective view of another embodiment of the game of the invention with a common display panel.

FIG. 4 is a diagrammatic detail illustration of an electronic matrix of the invention.

FIG. 5 shows diagramatically how the horizontal placement is transformed to vertical placement.

DETAILED DESCRIPTION OF PREFERRED EMBODIMENTS

Referring now first to FIG. 1, a compact, folding embodiment of the invention comprises three hinged-together panels 1, 2, 3 which lie parallel to one another when folded, for carrying by handle 4. The panels unfold to the configuration shown for playing with display panel 3 vertical, and opposed test panels 1, 2 horizontal for use by opposed players. Panel 3 shields opposing player's panels from direct view.

A visual, 2-dimensional planar display 9 on panel 3 may be visible from both sides of translucent panel 3. Alternatively, panel 3 may be opaque with a separate display on each face. The display may be any two-dimensional display such as those well known in the art including electroluminescent; liquid crystal; array of individual lights; or cathode ray tube.

Each of the test panels 1, 2 supports a touch-sensitive planar element 10, 11. The touch of a finger at any point on the plane generates an electrical signal indicating the two-dimensional coordinates x, y of the point in the plane. Touch sensitive planar elements are well known in the art, and may include for example, mechanical motion contactors, infrared sensor, surface acoustical wave sensors, capacitive coupling and the like, as exemplified by QuickPoint GX140 supplied by Microtouch Systems Inc. of Methuen, Mass.

A computer or microprocessor 5, powered by battery 6 or line cord 7, is connected to both touch-sensitive elements 10, 11, display 9, and timer 8.

Play begins when a first player, the testor, touches plane 10 at any point A. This is displayed at corresponding x, y coordinates on display 9, where it is visible to the second player, testee. At the time of display, timer 8 starts. The testee must then touch, as quickly as possible, plane 11 at a point B perceived to correspond, in the horizontal plane, to the displayed point A in the vertical plane. Simultaneously with the selection of point B, the timer stops and the time interval between display and response is recorded. The selected point B is displayed along with point A and the distance between, the error, is recorded. This may be done with a ruler or by a program within the computer 5 using, for example, a well known algorithm based on the Pythagorean theorem. Testee's score is computed from a combination of the response time and the error in any preselected algorithm such as by a simple addition (seconds plus centimeters). These methods are well known and need not be further described. The score is displayed on display 9. Players may alternate between being testor and testee for competition. When used for therapy or training, roles may be maintained, i.e. the therapist will always be the testor.

Referring now to FIG. 2, an alternative embodiment is illustrated in which test panels 2, 3 are disposed side by side with obscuring vertical panel 12 therebetween so that neither player can see the opponent's test panel. A vertical panel 3 is disposed beyond panel 12 where the display 9 thereon is visible to both players.

Referring now to FIG. 3, a game of the invention is shown employing well known elements of computer systems. A CRT Monitor 13 is connected to a conventional small computer 14 receiving a program on disc 15.

Any number of test panels 1, 2, 26 may be separated by obscuring panels 12. The test panels may bear touch-sensitive planar elements 10, 11 as described above. Alternatively, a mouse 16 may be employed at less expense to serve the testor for positioning the test point A. The game may be played with a solitary player, with the computer program, operating without human intervention, randomly positioning the test points or using a predetermined pattern of test points. The test points may be displayed at random time intervals to further test the response skills. The computer may display distracting information and images that are interrupted at random intervals by display of the test point, to further challenge a solitary player. The computer is programmed to display testor and testee points A and B, compute the error and the response time and display score on the display.

For a solitary player, this system may require only the touch-sensitive planar element 10 as the sole hardware addition along with programming. FIG. 4 shows how a matrix of horizontal wire contacts 17 may be superimposed on a matrix of vertical wires 18 in a touch-sensitive planar element 21 where finger pressure at selected points causes contact between the wires. Connections 19 to an array of lights display 20 causes a light to emit on the display at a point corresponding to the touched point on the touch-sensitive planar element 21.

FIG. 5 shows how the game may be played with transparent plastic plates 22, 23, and a vertical holder 24. A first player marks plate 22 with erasable mark R, and covers plate 22 with opaque cover sheet 25 so that opponent cannot see as covered plate 22 is placed vertically in holder 24. Timer 8 is started as sheet 25 is removed to display mark R. Opponent marks plate 23 at Q and stops timer. Plate 23 is then superimposed on plate 22 and placement error measured with a ruler and recorded along with response time. This embodiment of the game is least hardware intensive. A program embedded in computer (5) of FIG. 1 or disc (15) of FIG. 3 performs scoring as follows:

Input of X,Y of (10) in computer (5) or (14)

Display X,Y on display (9) and start clock (8) at $T_1$

Input $X_1,Y_1$ of (11) in computer and stop clock at $T_2$

Compute $T_2-T_1$=seconds to respond.

$$\text{Compute } \sqrt{(X_1-X)^2+(Y_1-Y)^2} = \text{Distance}$$

Display Distance+time and each separately.

The term point is used in its geometric sense as a unique location on a surface. It may be displayed by a simple pencil mark or a light or color on a monitor.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention within the scope of the appended claims.

I claim:

1. A game apparatus for testing spatial perception and physical response of a player comprising:

A) a planar, substantially vertical, display means for displaying visually to a player selected points in a vertical plane, said vertical planar display means having particular dimensions;

B) means for positioning, by means other than said player, a test point in said display means;

C) a planar, substantially horizontal, response means having dimensions corresponding to said particular dimensions, said response means for response positioning, by a player, a response point in a horizontal plane on said response means at a location perceived by said player as corresponding in two dimensions in said response means to the position of said test point when said test point is displayed to said player in said display means;

D) means for then displaying said response point on said vertical display means at a location corresponding to the position of said response point on the horizontal response means together with said test point; and E) means for measuring the error distance between said test and response points on said display means for scoring.

2. The game apparatus according to claim 1, further comprising:

timer means for measuring time interval between display to said player of said test point and said response positioning by said player.

3. The game apparatus according to claim 2, further comprising:

at least one additional horizontal response means, and in which any one of said horizontal response means may also be arranged to function as said means for positioning a, test point in said display means while other of said response means are employed for positioning said response point.

4. The game apparatus according to claim 2, in which said display means, said response means and said timer means are electrically powered and electrically interconnected.

5. The game apparatus according to claim 4, in which said response means is a touch-sensitive apparatus.

6. The game apparatus according to claim 6, in which said means for positioning said test point are entirely automatic.

7. The game apparatus according to claim 1, further comprising:

at least one additional horizontal response means, and in which any one of said horizontal response means may also be arranged to function as said means for positioning a first, test point in said display means while other of said response means are employed for positioning said response point.

8. The game apparatus according to claim 1, in which each player is provided with a separate response means shielded from the view of other players and each response means serves alternatively as means for positioning said test point or said response point.

9. A method of playing a spatial perception/physical response game for at least one player of the type which includes a vertical display for displaying points in a vertical plane and at least one planar horizontal response member having dimensions corresponding to the vertical display and the response member having means to position a point selected thereon onto the vertical display, the steps comprising:

A) displaying a test point or target on the vertical display to said at least one player;

B) said at least one player viewing the display with said test point thereon;

C) said at least one player indicating on said response member a response point at a location thereon perceived by said player to correspond to the test point or target viewed on the display;

D) transferring the response point on the response member to a corresponding location on the display along with the test point;

E) measuring the distance between test and response points on the display as a score.

10. The method according to claim 9, further comprising measuring the time interval between viewing the test point and indicating the response point on the response member to combine the time interval with said distance to derive a score.

11. A game apparatus for testing spatial perception and physical response of a player comprising:

A) a planar display means for displaying visually, in a substantially vertical plane, to a player, at least one target point, said display means having particular dimensions;

B) positioning means for positioning by means other than said player, said at least one target point in said display means;

C) a substantially horizontal planar response means having dimensions corresponding to said particular dimensions, said response means arranged for receiving a response point positioned on said response means by said player at a point thereon perceived by said player as corresponding in position in the horizontal plane to the position of said target point in the vertical plane as displayed to said player;

D) transfer means for displaying said response point from said response means onto said display means at a corresponding position thereon along with said target point; and E) means for measuring the error distance between said target and response points on said display means.

12. The game apparatus according to claim 11, further comprising timer means for measuring the time interval between display of said target point to said player and response of said player by positioning said response point on said response means.

\* \* \* \* \*